(12) United States Patent
Yasuda et al.

(10) Patent No.: US 7,601,873 B2
(45) Date of Patent: Oct. 13, 2009

(54) METHOD OF MANUFACTURING 3,3',4,4'-TETRAAMINOBIPHENYL

(75) Inventors: Hiroshi Yasuda, Minato-ku (JP); Orlov Varely Domitrovichi, Kharkov (UA)

(73) Assignee: Showa Denko K.K., Tokyo (JP)

( * ) Notice: Subject to any disclaimer, the term of this patent is extended or adjusted under 35 U.S.C. 154(b) by 0 days.

(21) Appl. No.: 12/327,506

(22) Filed: Dec. 3, 2008

(65) Prior Publication Data

US 2009/0149676 A1 Jun. 11, 2009

(30) Foreign Application Priority Data

Dec. 5, 2007 (UA) .............................. A200713592

(51) Int. Cl.
*C07C 211/00* (2006.01)
(52) U.S. Cl. ..................................................... 564/309
(58) Field of Classification Search .................. 564/309
See application file for complete search history.

(56) References Cited

U.S. PATENT DOCUMENTS 5,041,666 A * 8/1991 Ward et al. ................... 564/309
6,835,854 B1 * 12/2004 Maner et al. ................. 564/309
6,979,749 B2 * 12/2005 Bavikar et al. ............... 564/309

* cited by examiner

*Primary Examiner*—Jafar Parsa
(74) *Attorney, Agent, or Firm*—Sughrue Mion, PLLC

(57) ABSTRACT

An object of the present invention is to provide an efficient method of manufacturing 3,3',4,4'-tetraaminobiphenyl with a smaller number of steps. The manufacturing method of 3,3',4,4'-tetraaminobiphenyl includes reacting the amino groups of a 4-halo-o-phenylenediamine with an inorganic sulfur compound to lead to a 5-halo-2,1,3-benzothiadiazole, subsequently coupling two molecules of the benzothiadiazole together to form a 5,5'-bis(2,1,3-benzothiadiazole) and then deprotecting the amino groups to yield 3,3',4,4'-tetraaminobiphenyl.

4 Claims, No Drawings

METHOD OF MANUFACTURING 3,3',4,4'-TETRAAMINOBIPHENYL

BACKGROUND OF THE INVENTION

1. Field of the Invention

The present invention relates to a method of manufacturing 3,3',4,4'-tetraaminobiphenyl in an effective manner.

2. Background Art 3,3',4,4'-Tetraaminobiphenyl is an industrially important compound as a raw material for heat resistant polymers, dyes, electronic materials and the like.

Various methods are known as a general manufacturing method for this 3,3',4,4'-tetraaminobiphenyl. Examples of such methods include a benzidine method (Non-patent Document 1), a biphenyl method (Patent Document 1), a dichlorobenzidine method (Patent Document 2) and a coupling method (Patent Document 3).

(Benzidine Method)

The benzidine method is a classical method of manufacturing 3,3',4,4'-tetraaminobiphenyl using benzidine as a raw material. A series of several steps are used to synthesize 3,3',4,4'-tetraaminobiphenyl starting with benzidine (4,4'-diaminobiphenyl).

That is, amino groups in benzidine are first protected by N-acetylation with acetic anhydride, and the resulting acetylated compound is then converted into 3,3'-dinitro-N,N'-diacetylbenzidine by nitration. For example, this nitration is performed with concentrated nitric acid in a mixture of acetic anhydride and acetic acid. 3,3'-Dinitro-N,N'-diacetylbenzidine is treated with a base to remove the acetyl groups and then treated with tin (II) chloride in hydrochloric acid to reduce the nitro groups to yield 3,3',4,4'-tetraaminobiphenyl (Scheme 1).

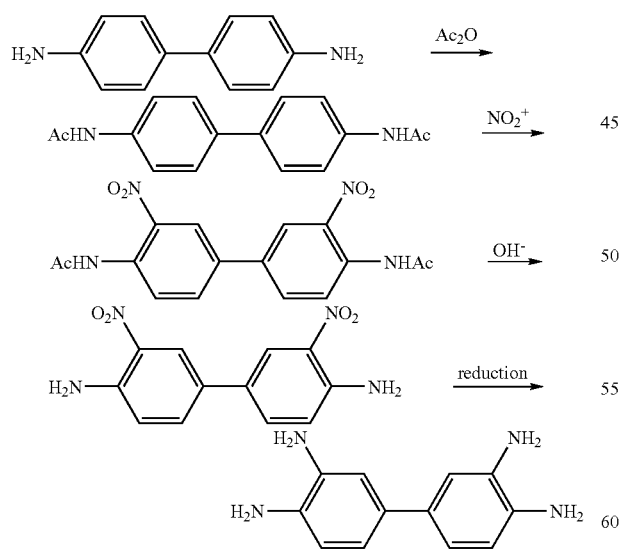

(Biphenyl Method)

A method according to Patent Document 1 is known as an improved method of manufacturing 3,3',4,4'-tetraaminobiphenyl starting with biphenyl as a raw material.

Biphenyl is first diacylated with acetyl chloride under a Friedel-Crafts condition. 4,4'-Diacetylbiphenyl obtained is then treated with hydroxylamine to give a corresponding oxime, which is further converted into N,N'-diacetylbenzidine in the presence of an acid via Beckmann rearrangement. After that, this compound is successively subjected to nitration, deprotection by a base and then reduction of the nitro groups to yield 3,3',4,4'-tetraaminobiphenyl in the same manner as in the above benzidine method (Scheme 2).

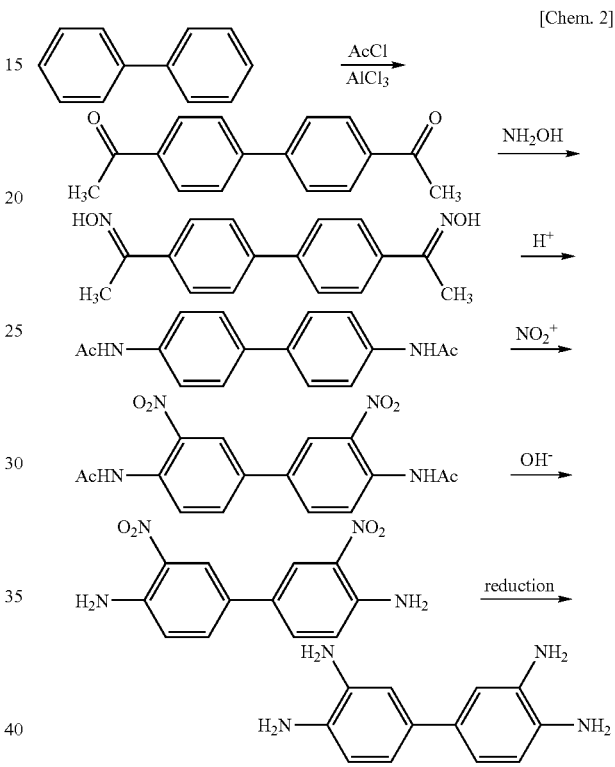

(Dichlorobenzidine Method)

A method according to Patent Document 2 is known as a method directly utilizing a benzidine skeleton. 3,3'-Dichlorobenzidine is treated with ammonia in the presence of a copper catalyst at high temperature (150 to 250° C.) and high pressure (1 to 10 MPa) to yield 3,3',4,4'-tetraaminobiphenyl (Patent Document 2, Scheme 3).

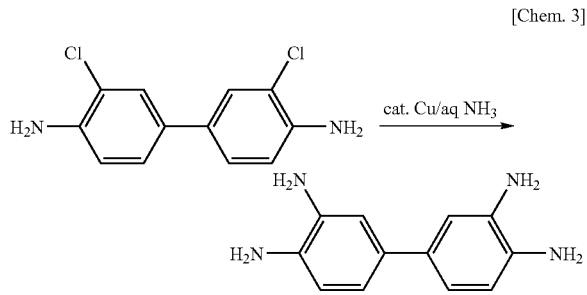

(Coupling Method)

A method according to Patent Document 3 can be listed as a manufacturing method for 3,3',4,4'-tetraaminobiphenyl not using the benzidine skeleton as a starting material. This method uses Suzuki's coupling between 4-acetylamino-3-nitrobromobenzene and 4-acetylamino-3-nitrophenyl borate to form the benzidine skeleton, followed by deprotection with a base and reduction of the nitro groups in turn to yield 3,3',4,4'-tetraaminobiphenyl.

Scheme 4

[Chem. 4]

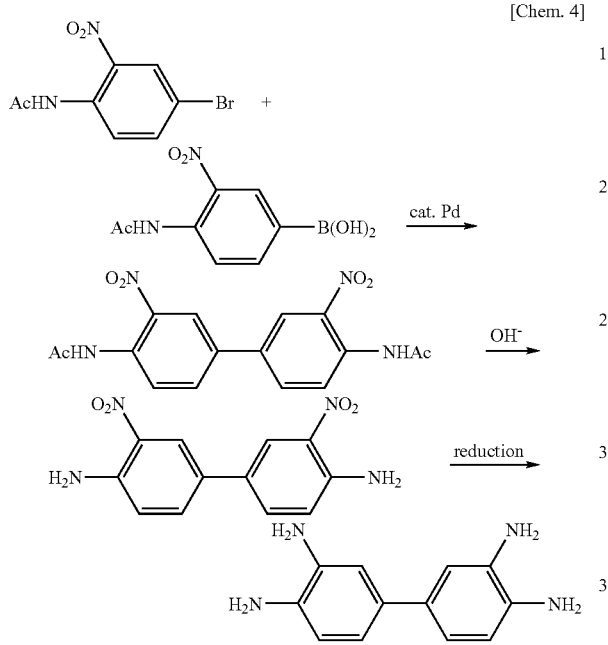

Patent Document 1: U.S. Pat. No. 5,041,666
Patent Document 2: Japanese Patent Laid-Open Publication No. 2004-161643
Patent Document 3: U.S. Patent Application No. 2005/0215823
Non-patent Document 1: H. Vogel, C. S. Marvel, J., Polym. Sci., 50, 511 (1961)
Non-patent Document 2: I. A. Belenkaya, T. A. Shulla, J. Heterocyclic Chem. 11, 1555-1558 (1989)

However, the above benzidine method has a problem that it involves likelihood of deterioration of working conditions and pollution of the environment, because benzidine, which is the starting material, is a carcinogen.

The above biphenyl method is inefficient, since it requires many steps and heavy use of a stoichiometric quantity of reagents in order to obtain 3,3',4,4'-tetraaminobiphenyl.

The above dichlorobenzidine method has problems that it requires special attention to deterioration of working conditions and environmental pollution because dichlorobenzidine used is a mutagen, and that it requires special manufacturing facilities because the reaction in the presence of ammonia requires a high temperature and a high pressure.

Moreover, the above-mentioned coupling method additionally requires Grignard reaction and the like to synthesize a borate compound as the starting material for the coupling reaction as well as an expensive palladium catalyst for the coupling reaction. There is thus a problem that it requires steps for catalyst recovery, recycling and the like to complicate the process as a whole and increase a manufacturing cost.

An object of the present invention is thus to provide a manufacturing method capable of efficiently producing 3,3',4,4'-tetraaminobiphenyl through a smaller number of steps. A starting material different from those used in the conventional manufacturing methods is chosen to eliminate use of highly toxic or carcinogenic substances, thus allowing improvement of working conditions and safer environment.

SUMMARY OF THE INVENTION

The present inventors have earnestly studied to address the above problems and found a manufacturing method of 3,3',4,4'-tetraaminobiphenyl, which includes protection of the amino groups of a 1,2-diamino-4-halobenzene as a starting material, a subsequent coupling reaction to form a carbon-carbon bond and deprotection of the amino groups to yield 3,3',4,4'-tetraaminobiphenyl, completing the present invention.

That is, the present invention relates to following terms [1] to [4].

[1] A method of manufacturing 3,3',4,4'-tetraaminobiphenyl, comprising:

reacting amino groups of a phenylenediamine compound represented by the following formula (1) with an inorganic sulfur compound,

[Chem. 5]

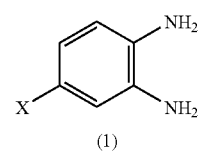

(1)

(in which X represents a chlorine, bromine or iodine atom) to form a benzothiadiazole compound represented by the following formula (2),

[Chem. 6]

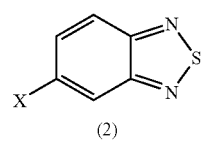

(2)

(in which X represents a chlorine, bromine or iodine atom); coupling two molecules of the compound (2) together to yield 5,5'-bis(2,1,3-benzothiadiazole) represented by the following formula (3); and

[Chem. 7]

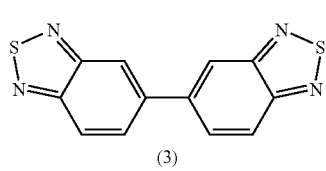

(3)

deprotecting the amino groups to obtain 3,3',4,4'-tetraaminobiphenyl represented by the following formula (4).

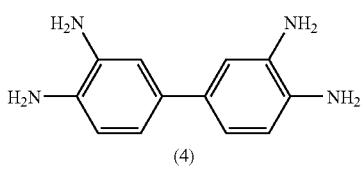

(4)

[2] The manufacturing method according to above term 1, wherein the coupling reaction is carried out in the presence of metallic copper.
[3] The manufacturing method according to above term 1 or 2, wherein the deprotection of the amino groups is carried out under a reductive condition.
[4] The manufacturing method according to above term 1 or 2, wherein the deprotection of the amino groups is carried out by reduction with a metal.

EFFECT OF THE INVENTION

The manufacturing method of the present invention enables efficient manufacture of 3,3',4,4'-tetraaminobiphenyl using a smaller number of steps. No need to use highly toxic starting materials enables improvement of working conditions and safer environment.

DESCRIPTION OF THE PREFERRED EMBODIMENTS

The present invention is detailed in the following.
A 4-halo-o-phenylenediamine is used as a starting material in the method of manufacturing 3,3',4,4'-tetraaminobiphenyl of the present invention. Examples of the 4-halo-o-phenylenediamine include 4-chloro-o-phenylenediamine and 4-bromo-o-phenylenediamine.

<Protection of Amino Groups in the 4-Halo-o-phenylenediamine>

In the present invention, the amino groups are first protected by reacting the 4-halo-o-phenylenediamine represented by the above formula (1) with an inorganic sulfur compound to yield a 5-halo-2,1,3-benzothiadiazole represented by the above formula (2). In the 4-halo-o-phenylenediamine used in the present invention, the halogen is chlorine, bromine or iodine.

In the present invention, a coupling reaction of the 4-halo-o-phenylenediamine is used to build the benzidine skeleton. When the coupling reaction is carried out without protecting the amino groups of the 4-halo-o-phenylenediamine, diphenylamine may be formed as a byproduct. Accordingly these amino groups are protected prior to the coupling reaction with a functional group/functional groups which is/are not removed in the coupling reaction.

An amide group, a carbamoyl group, an N-sulfonyl group, a sulfonamide group or the like may be used here as such a protective group. It is preferred to derive a thiadiazole ring from the amino groups for their protection. For example, a method based on the method according to the above Nonpatent Document 2 is preferred to protect the amino groups.

That is, an inorganic sulfur compound is used when the above amino groups are converted to the thiadiazole ring. The inorganic sulfur compounds employable in the invention include inorganic divalent sulfur compounds such as sulfur dichloride and inorganic tetravalent sulfur compounds such as thionyl chloride. Among them, thionyl chloride is preferred. At least an equivalent mole of the above sulfur-containing compound relative to one mole of the 4-halo-o-phenylenediamine should be used, but the sulfur-containing compound is preferably used in excess so that the reaction will complete.

A solvent may be used in the present reaction if necessary. The solvent may serve to dissolve or disperse the 4-halo-o-phenylenediamine for effective contact with the inorganic sulfur compound, to prevent rapid and drastic reaction by dilution effect, and to absorb liberated heat by reflux. In the present invention, hydrocarbon solvents such as hexane, cyclohexane, methylcyclohexane, heptane and octane; aromatic hydrocarbon solvents such as benzene, toluene, xylene and ethylbenzene; and halogenated solvents such as dichloromethane, chloroform, dichloroethane, trichloroethane, tetrachloroethane, chlorobenzene and dichlorobenzene may be used. Among them, the aromatic hydrocarbon solvents are preferably used. The amount of the solvent used is preferably 2 to 50 times by weight, more preferably 5 to 30 times by weight that of the 4-halo-o-phenylenediamine.

However, when thionyl chloride is used as the inorganic sulfur compound, it can serve also as the solvent. In this case, the amount of thionyl chloride used is 1.5 to 10 times by weight that of the 4-halo-o-phenylenediamine.

An acid may be used to accelerate the present reaction if necessary. In the present invention, nonvolatile protonic acids are preferably used. Among them, sulfuric acid is particularly preferred. The amount of the acid used is 0.01 to 1.0 times by weight, preferably 0.1 to 0.3 times by weight that of the 4-halo-o-phenylenediamine.

The present reaction is performed under air or an inert atmosphere such as nitrogen.

The present reaction is generally carried out by mixing the 4-halo-o-phenylenediamine and the inorganic sulfur compound, adding the solvent and the acid if necessary, and heating and stirring. When a gas such as hydrogen chloride is generated in the reaction, the gas is preferably collected with an alkali trap outside a reaction vessel. The present reaction is generally carried out at a temperature of from 80° C. to a reflux temperature of the reaction solution. In the present invention, the reaction is preferably carried out at a reflux temperature of the reaction solution.

<Coupling Reaction>

Next, in the present reaction, two molecules of the 5-halo-2,1,3-benzothiadiazole (2) obtained in the above protective reaction are coupled together to yield 5,5'-bis(2,1,3-benzothiadiazole) (3). The 5,5'-bis(2,1,3-benzothiadiazole) (3) is a precursor compound for 3,3',4,4'-tetraaminobiphenyl.

Although various known methods for such coupling reaction maybe used so long as a desired purpose is achieved, in the present invention, the Ulmann reaction, which uses metallic copper as a coupling agent, is preferred in the coupling reaction from a perspective of reaction simplicity and economy.

Copper used in the present invention is preferably in a form of granular copper, specifically copper shavings, copper dust, copper powder, and the like from a perspective of reaction efficiency. Copper should be used at least in an equimolar amount to the 5-halo-2,1,3-benzothiadiazole compound has to be used. However, excess amount of copper relative to that of the 5-halo-2,1,3-benzothiadiazole compound is preferably used to ensure completion of the reaction. On the other hand, considering the balance between promotion of the coupling reaction and removal of unreacted copper at the end of the reaction, copper is preferably used in slight excess over the 5-halo-2,1,3-benzothiadiazole compound. Based on this, the amount of copper used in the present coupling reaction is 1.01 to 2 moles, preferably 1.1 to 1.6 moles relative to one mole of the 5-halo-2,1,3-benzothiadiazole compound.

Amide solvents such as dimethylformamide, diethylformamide, dimethylacetamide and N-methylpyrrolidone, and nitrobenzene solvents such as nitrobenzene and nitrotoluene may be used for the coupling reaction in the present reaction. In the present invention, the amide solvent is preferably used and dimethylformamide is particularly preferred. The amount of the solvent used is 2 to 50 times, preferably 3 to 30 times by weight that of copper used.

The present reaction is generally carried out under an inert atmosphere such as nitrogen or argon.

The above coupling reaction is generally carried out by mixing the solvent such as dimethylformamide with the 5-halo-2,1,3-benzothiadiazole compound and copper and heating the mixture. The reaction temperature generally ranges from 100° C. to a reflux temperature of the reaction solution.

<Deprotection>

5,5'-bis(2,1,3-benzothiadiazole) thus obtained is deprotected to yield 3,3',4,4'-tetraaminobiphenyl. Various methods may be used for deprotection of the amino groups in the benzothiadiazole. Deprotection is preferably carried out under a reductive condition in order not to impair the amino groups formed.

Hydrogen reduction with a metal catalyst, reduction with a metal and the like may be used as the reduction method. Reduction with a metal is preferred. Example of the metals include typical metals such as sodium, potassium, magnesium, aluminum and transition metals such as iron, zinc and tin. Magnesium and zinc are preferred. A source to supply protons is required for this reaction and a protic solvent such as water or alcohol, or an acid such as hydrochloric acid is added to supply protons. Twelve electrons are herein required to reduce 5,5'-bis(2,1,3-benzothiadiazole) and the electrons used in this reaction are supplied from the metal (the following formula (A)). For example, when zinc or magnesium, which is a divalent metal, is used, at least 6 moles of such metal relative to one mole of 5,5'-bis(2,1,3-benzothiadiazole) have to be used. However, excess amount of such metal relative to a theoretical quantity is preferably used to ensure completion of the reaction. Accordingly, 6 to 80 moles of such metal relative to one mole of 5,5'-bis(2,1,3-benzothiadiazole) is preferably used.

[Chem. 9]

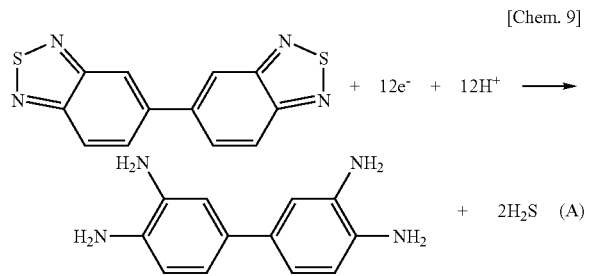

The metal used in the present invention is preferably in a form of granules, shavings, dust, powder, and the like from a perspective of improving reaction efficiency.

In the deprotection, a solvent may be used without limitation. Suitable solvents include protic solvents such as water, alcohols and organic acids. Methanol, ethanol, propanol, butanol, and the like are used as the alcohols, while formic acid, acetic acid, propionic acid, and the like are used as the organic acids. The amount of the solvent used is 2 to 50 times, preferably 5 to 30 times by weight that of 5,5'-bis (2,1,3-benzothiadiazole).

The present reaction is carried out under air or an inert atmosphere such as nitrogen or argon.

The reaction is generally carried out by dissolving 5,5'-bis (2,1,3-benzothiadiazole) in the solvent such as an alcohol, adding the acid if necessary and further adding and mixing the metal. The reaction temperature generally ranges from 0° C. to a reflux temperature of the reaction fluid.

EXAMPLES

The present invention is specifically described with illustration of the following Examples, but not limited in any way by these Examples.

Gas chromatography (analytical instrument: model 6890N manufactured by Agilent Technologies, Ltd., analysis column: DB-1 column manufactured by J&W Scientific Inc.) was in principle used for analysis of each component in the Examples. High performance liquid chromatography (analytical instrument: model LC-2010HT manufactured by SHIMADZU Co., analysis column: RP-18 (ODS) column with endcapping treatment manufactured by Kanto Chemical Co. Inc.) was used for analysis of low volatile substances.

Example 1

Synthesis of 5-chloro-2,1,3-benzothiadiazole

A mixture was prepared by mixing 4.0 g (28 mmol) of 4-chloro-o-phenylenediamine, 14 mL of thionyl chloride and 0.62 mL of concentrated sulfuric acid and was refluxed for one hour. This mixture was cooled and then poured onto ice, and a resultant precipitate was filtered and collected. This precipitate was washed with water till the waste water became neutral and then thoroughly dried to yield 4.6 g of 5-chloro-2,1,3-benzothiadiazole as a crude product (melting point, 50 to 54° C.; yield, 96%). This crude product was vacuum-distilled to yield a pure product of 5-chloro-2,1,3-benzothiadiazole (melting point, 54° C.; yield, 85%).

Synthesis of 5,5'-bis(2,1,3-benzothiadiazole)

A reaction mixture of 2.2 g (12.9 mmol) of 5-chloro-2,1, 3-benzothiadiazole and 1.3 g (20.5 mmol) of copper powder was heated in 5 mL of dimethylformamide with stirring at 150° C. for 20 hours. This reaction mixture was cooled and then poured into water (40 mL), and a resulting precipitate was filtered and collected. After this precipitate was dried, it was extracted with benzene (20 mL×3). After combining these benzene extracts, the combined extract was dried under vacuum to complete dryness. A resulting oily residue was triturated with petroleum ether, and a mother liquor was removed to yield 1.45 g of 5,5'-bis(2,1,3-benzothiadiazole) (melting point, 61 to 62° C.; yield, 83%).

Synthesis of 3,3',4,4'-tetraaminobiphenyl

A methanol solution (20 mL) containing 1.0 g (3.7 mmol) of 5,5'-bis (2,1,3-benzothiadiazole) was heated to 45° C., to which 1.6 g (65.8 mmol) of metallic magnesium powder was added in one hour with stirring and then the resulting mixture was heated at 60° C. for 20 minutes. After unreacted magnesium was removed by filtration and methanol was distilled off, isobutyl methyl ether (10 mL) and a saturated aqueous ammonium chloride solution (20 mL) were added to the residue. The resulting mixture was stirred for 10 minutes. An organic layer was separated, dried over anhydrous sodium sulfate and then concentrated to dryness. This concentrated residue was dissolved in water (20 mL) containing concentrated hydrochloric acid (5 mL). The resulting solution was cooled to precipitate crystals, which were collected by filtration and dried to yield 1.07 g of 3,3',4,4'-tetraaminobiphenyl hydrochloride (yield, 80%).

Example 2

Synthesis of 5-bromo-2,1,3-benzothiadiazole

A mixture was prepared by mixing 4.0 g (21 mmol) of 4-bromo-o-phenylenediamine, 14 mL of thionyl chloride and 0.62 mL of concentrated sulfuric acid and was refluxed for one hour. This mixture was cooled and then poured onto ice, and a resulting precipitate was filtered and collected. This precipitate was washed with water till the waste water became neutral and then thoroughly dried to yield 4.5 g of 5-bromo-2,1,3-benzothiadiazole as a crude product (melting point, 48 to 50° C.; yield, 96.5%). This crude product was vacuum-distilled to yield a pure product of 5-bromo-2,1,3-benzothiadiazole (melting point, 50° C.; yield, 86%).

Synthesis of 5,5'-bis(2,1,3-benzothiadiazole)

A reaction mixture prepared by adding 4.6 g (21.4 mmol) of 5-bromo-2,1,3-benzothiadiazole and 2 g (31.5 mmol) of copper powder to 10 mL of dimethylformamide was heated with stirring at 150° C. for 6 hours. This reaction mixture was cooled and then poured into water (40 mL), and a resulting precipitate was filtered and collected. After this precipitate was dried, it was extracted with benzene (20 mL×3). After combining these benzene extracts, the combined extract was dried under vacuum to complete dryness. A resulting oily residue was triturated with petroleum ether, and a mother liquor was removed to yield 2.1 g of 5,5'-bis(2,1,3-benzothiadiazole) (melting point, 61 to 62° C.; yield, 73%).

Synthesis of 3,3',4,4'-tetraaminobiphenyl

A reaction mixture prepared by adding 2.5 g (38.2 mmol) of zinc suspended in 6 mL of a 20% aqueous hydrochloric acid solution to a 20% aqueous hydrochloric acid solution (6 mL) containing 1.0 g (3.7 mmol) of 5,5'-bis(2,1,3-benzothiadiazole) was refluxed for 1.5 hours with stirring. The reaction mixture was cooled and filtered. While the filtrate was concentrated crystals started precipitating. This concentrated solution was cooled to collect the crystals by filtration to yield 1.0 g of 3,3',4,4'-tetraaminobiphenyl hydrochloride (melting point, 265 to 267° C.; yield, 75%).

What is claimed is:

1. A method of manufacturing 3,3',4,4'-tetraaminobiphenyl, comprising:
reacting amino groups of a phenylenediamine compound represented by the following formula (1) with an inorganic sulfur compound,

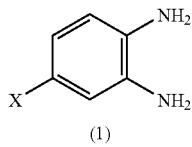

[Chem. 1]

(wherein X represents a chlorine, bromine or iodine atom) to form a benzothiadiazole compound represented by the following formula (2),

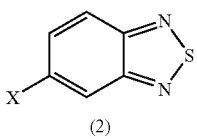

[Chem. 2]

(wherein X represents a chlorine, bromine or iodine atom); coupling two molecules of the compound (2) together to yield 5,5'-bis(2,1,3-benzothiadiazole) represented by the following formula (3); and

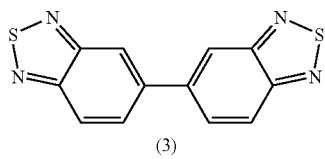

[Chem. 3]

deprotecting the amino groups to obtain 3,3',4,4'-tetraaminobiphenyl represented by the following formula (4)

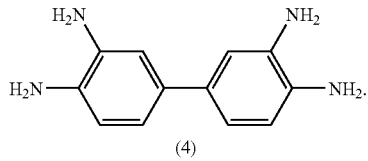

[Chem. 4]

2. The manufacturing method according to claim 1, wherein the coupling reaction is carried out in the presence of metallic copper.

3. The manufacturing method according to claim 1 or 2, wherein the deprotection of the amino groups is carried out under a reductive condition.

4. The manufacturing method according to claim 1 or 2, wherein the deprotection of the amino groups is performed by reduction with a metal.

* * * * *